United States Patent [19]
Lai et al.

[11] Patent Number: 5,512,472
[45] Date of Patent: Apr. 30, 1996

[54] DNA SEQUENCE ENCODING STEROL Δ14 REDUCTASE

[75] Inventors: Margaret H. K. Lai, E. Brunswick; Donald R. Kirsch, Princeton, both of N.J.; Martin Bard, Carmel, Ind.

[73] Assignee: American Cyanamid Company, Wayne, N.J.

[21] Appl. No.: 439,131

[22] Filed: May 11, 1995

Related U.S. Application Data

[63] Continuation of Ser. No. 107,347, Aug. 16, 1993, abandoned.

[51] Int. Cl.[6] .............................. C12N 9/02; C12N 15/53; C12N 15/81; C12N 15/09
[52] U.S. Cl. .................. 435/240.1; 435/69.1; 435/172.3; 435/198; 435/252.3; 435/254.21; 435/320.1; 536/23.2; 935/14; 935/28; 935/69
[58] Field of Search .......................... 536/23.2; 435/69.1, 435/172.3, 252.3, 254.21, 320.1, 240.1

[56] References Cited

PUBLICATIONS

Ashman, W. H., et al., Lipids 26: 628–632 (1991).
Baloch, R. and Mercer, I., Phytochemistry 26: 663–668 (1987).
Balzi, E., et al., J. Biol. Chem. 262: 16871–16879 (1987).
Brugge, J. S., et al., Mol. Cell. Biol. 7:2180–2187 (1987).
Chen, W., et al., Yeast 7: 305–308 (1991).
Gaber, R. F., et al., Mol. Cell. Biol. 9: 3447–3456 (1989).
Kyte, J., and Doolittle, R. F., J. Mol. Biol. 157: 105–132 (1982).
Lorenz, T., and Parks, L. W., DNA and Cell Biol. 11: 685–692 (1992).
Marcireau, C., et al., Curr. Genet. 22: 267–272 (1992).
Molzahn, S. W., and Woods, R. A., J. Gen Microbiol. 72: 339–348 (1972).
Nasmyth, K. A., and Tatchell, K., Cell 19: 753–764 (1980).
Paltauf, F., et al., in Jones, E. W., et al., eds., The Molecular and Cellular Biology of the Yeast Saccharomyces, Gene Expression, Cold Spring Harbor Laboratory Press, 1992, pp. 415, 418–420, 424–428, and 434–437.
Shimanuki, M., et al., Mol. Biol. Cell 3: 263–273 (1992).
Worman, H. J., et al., J. Cell Biology 111: 1535–1542 (1990).

*Primary Examiner*—Robert A. Wax
*Assistant Examiner*—William W. Moore
*Attorney, Agent, or Firm*—Darryl L. Webster; Mary M. Krinsky

[57] ABSTRACT

A gene encoding *Saccharomyces cerevisiae* sterol Δ14 reductase of the ergosterol biosynthetic pathway is isolated and cloned by selecting strains carrying sequences on a 2μ based vector for resistance to a morpholine fungicide such as fenpropimorph. Four distinct plasmid inserts which produce morpholine resistance are obtained, and one of these is characterized and sequenced. The purified and isolated DNA sequence encoding sterol Δ14 reductase encodes a polypeptide exhibiting homology to the *S. cerevisiae* sterol C-24(28) reductase enzyme in the ergosterol biosynthetic pathway.

13 Claims, 4 Drawing Sheets

PML100
LAMBR
YGL022
ST SL

PML100  N P R T T E F E F G G L I G A L G I S I G L P V F T I I L
LAMBR   S S K T K E L E F G G R F G T F M L M F F L P A T V L Y L
YGL022  K P N E I E Y E F G G T T G V I G M L I G F P L L M Y Y M
ST SL   V K K S A P R E F G G A K G A L A I M T G F P C L M Y Y L

PML100  K P L R Y Y L G N R E L W T V Y C L W Y G I L A V L D V I
LAMBR   L P A L E S L W E T K V F G V F L L W F F F Q A L F Y L L
YGL022  L V L E N G I P E K Y D W T I F L T F W V F Q I I F Y Y T
ST SL   Y I Y V G A Y P T R Y A F L V F W S F C I V Q A V M Y L T

PML100  L V L A I R W K L T D G Q L P E L Q Y L Y E N H V S L C I
LAMBR   L T A A A I Q T L L Y F Q F - E L H Y L Y D H F V Q F A V
YGL022  L Y V T T T L V L V L H F T N L F R L Y V I I D R F G R I
ST SL   F Y T T I V I L A V L H V T H V F P I T T F I D M F G P L

PML100  E K I L A L G G N S G N I I Y D W F I G R E L N P R L G P
LAMBR   E E D L A P G G N S G Y L V Y N F F T G H E L N P R I G S
YGL022  F I S H D Y H R M T G N H L Y D F F M G A P L N P R W G I
ST SL   R L F D K P H R L S G N P I Y D A F M G A C L N P R L G K

PML100  K T G K I N D A L V L V N F L Q G F Y I F D G V L N E E G
LAMBR   N Q S M P S L S M I L V N S F Q L L Y V V D A L W N E E A
YGL022  T Y G Y V T P Q L G V V M L A H W L Y A N A C A K G E E L
ST SL   T Y G T V S P Q V L F V C L G H Y L Y A N A C S K G E Q L

PML100  A R Y L S V S P V E L G W V K V V G - - - I L A I M F L G
LAMBR   A F Y I V G H P I A I S W P V A A A - - - I T I L N C I G
YGL022  T L Y L Y Y H D P S E Y H W S T L Y N V S L Y V V L L C A
ST SL   T L Y L F S H D P S V Y N W S T Q Y T T G I Y V L L L C C

PML100  Q G K L E N L K S I Q T K R G T K L L C D G W W A K S Q
LAMBR   A D P K L S Y L K V I P T A T G K G L L V T G W W G F V R
YGL022  P Y Q I L K N P K Y M V T S N G S Y L L I D G W Y T L A R
ST SL   P W L I I K N P T F I R C A N G G T L L T S G W Y R Y A R

PML100  F A T L L L H R Q Q R D E H K C R L K Y G E N W E E Y E R
LAMBR   E I C L L V H R E A R D E H H C K K K Y G L A W E R Y C Q
YGL022  I L V V L I H R A F R D Q A K C K R K Y G K D W D E Y C K
ST SL   I F V V L V H R V S R D I K K C K A K Y G A D F D E Y D R

DNA SEQUENCE ENCODING STEROL Δ 14 REDUCTASE

This is a continuation of application Ser. No. 08/107,347 filed on Aug. 16, 1993, now abandoned.

TECHNICAL FIELD OF THE INVENTION

This invention relates to the identification of a *Saccharomyces cerevisiae* gene encoding sterol Δ14 reductase.

BACKGROUND OF THE INVENTION

Sterols are steroid alcohols of vegetable and animal origin. Ergosterol is the principal membrane sterol of fungi. It is structurally similar to its animal counterpart, cholesterol, and its higher plant counterparts, stigmasterol and sitosterol. Though the biosynthesis of ergosterol in fungi involves steps distinct from the other sterols, the pathways in different organisms share several common steps. The lanosterol 14α-demethylation steps in cholesterol and ergosterol formation in animals and fungi, as well as the obtusifoliol 14α-demethylation in stigmasterol and sitosterol biosynthesis in plants, both lead to the formation of a double bond between carbons 14 and 15 of the sterol ring. This double bond is then reduced by sterol Δ14 reductase activity. The enzyme is located in the microsomal fraction in pig liver, yeast and *Zea mays*, and requires NADPH as an electron donor (Marcireau, C., et al., *Curr. Genet.* 22: 267–272 (1992)).

Genetic studies of ergosterol biosynthesis mainly have been carried out in Saccharomyces cerevisiae (Paltauf, F., et al., in Jones, E. W., et al., eds., *The Molecular and Cellular Biology of the Yeast Saccharomyces, Gene Expression*, Cold Spring Harbor Laboratory Press, 1992, pages 434–437). In yeast, ergosterol affects membrane fluidity and permeability and plays an essential role in the yeast cell cycle.

A number of mutations in the yeast ergosterol biosynthetic pathway have been isolated either by reverse genetic approaches or by selection for mutations producing polyene resistance, and many of the genes have been identified. Toward the end of the pathway, sterol Δ14 reductase, Δ8–Δ7 isomerase, and C-24(28) reductase catalyze steps in the conversion of lanosterol to ergosterol. After ignosterol is reduced by sterol Δ14 reductase, which eliminates a double bond in the D ring of the molecule, the sterol is demethylated and rearranged to fecosterol, which is then isomerized by sterol Δ8–Δ7 isomerase. The sterol is then desaturated in two positions and its side chain is reduced by C-24(28) reductase. Some of the genes encoding the enzymes have been identified and named as follows (Paultauf, et al., cited above, Lorenz, T., and Parks, L. W., *DNA and Cell Biol.* 11: 685–692 (1992), and Example 1 below):

| Enzyme | Gene |
| --- | --- |
| Δ14 reductase | ERG24 |
| C-24 methyl transferase | ERG6 |
| Δ8–Δ7 isomerase | ERG2 |
| C-24(28) reductase | ERG4 |

Based on the accumulation of intermediates following fungicide treatment, morpholine fungicidal compounds such as tridemorph and fenpropimorph have been reported to be inhibitors of sterol 14 reductase and sterol Δ8–Δ7 isomerase (Baloch, R. and Mercer, I., *Phytochemistry* 26: 663–668 (1987)). However, it recently has been found that the sterol Δ8–Δ7 isomerase gene is not essential for viability in *S. cerevisiae* (Ashman, W. H., et al., *Lipids* 26: 628–632 (1991)), suggesting that the killing effect of morpholine fungicides may be primarily the result of sterol Δ14 reductase inhibition.

It has also been shown that the C-24 methyl transferase gene (ERG6) is not essential for viability in *S. cerevisiae* (Gaber, R. F., et al., *Mol. Cell. Biol.* 9: 3447–3456 (1989)). Mutant cells exhibit normal vegetative growth, but they differ from the wildtype in a number of respects, including drug supersensitivity, presumably due to alterations in membrane function (ibid.). Drug super-sensitivity has been observed in other yeast mutants, including one denoted YGL022 which encodes a putative transport protein (Chen, W., et al., *Yeast* 7: 305–308 (1991)).

SUMMARY OF THE INVENTION

The objects of the invention are to identify a gene encoding sterol Δ14 reductase, to elucidate the primary structure of the enzyme encoded by the gene, and to investigate the relationship of the structure to other polypeptides, especially other enzymes in the sterol biosynthetic pathway. The sterol Δ14 reductase gene and enzyme are useful in devising screening tests to identify sterol biosynthesis inhibitors that are potential fungicides for a wide variety of agricultural, medical, and veterinary applications.

These and other objects are accomplished by the present invention, which provides a gene encoding sterol Δ14 reductase, the polypeptide primary structure it encodes, and the relationship of the structure to other polypeptides. Also provided are RNA sequences corresponding to the DNA sequence of the gene, biologically functional plasmids or vectors comprising the DNA or RNA sequence, and procaryotic or eucaryotic host cells transformed or transfected with the plasmid or vector in a manner allowing the host cell to express the polypeptide.

A DNA sequence encoding *Saccharomyces cerevisiae* sterol Δ14 reductase is cloned by selecting strains carrying sequences on a 2μ based vector for resistance to a morpholine fungicide such as fenpropimorph, fenpropidin, or tridimorph. Fenpropimorph is preferred. When fenpropimorph is employed, four distinct plasmid inserts which produce morpholine resistance are obtained, denoted pML99, pML100, pML101 and pML103, which are useful in screens of sterol biosynthesis inhibition. One of these, pML100, is characterized and sequenced, and the putative amino acid sequence of the polypeptide encoded by the open reading frame is determined (SEQ ID NO 2).

DESCRIPTION OF THE FIGURES

FIG. 3 depicts a comparison of the amino acid sequence derived from the major open reading frame of the pML100 sequence encoding *S. cerevisiae* sterol Δ14 reductase (SEQ ID NO 2) with three homologous sequences: the chicken nuclear lamin B receptor (SEQ ID NO 3, Worman, H. J., et al., *J. Cell Biology* 111: 1535–1542 (1990)), the *Saccharomyces cerevisiae* YGL022 sequence (SEQ ID NO 4, Chen, et al., cited above), and the *Schizosaccharomyces pombe* sts1 gene (SEQ ID NO 5, Shimanuki, M., et al., *Mol. Biol. Cell* 3: 263–273 (1992)). The figure employs standard one-letter nomenclature for the amino acids: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

DETAILED DESCRIPTION OF THE INVENTION

Figure 1:
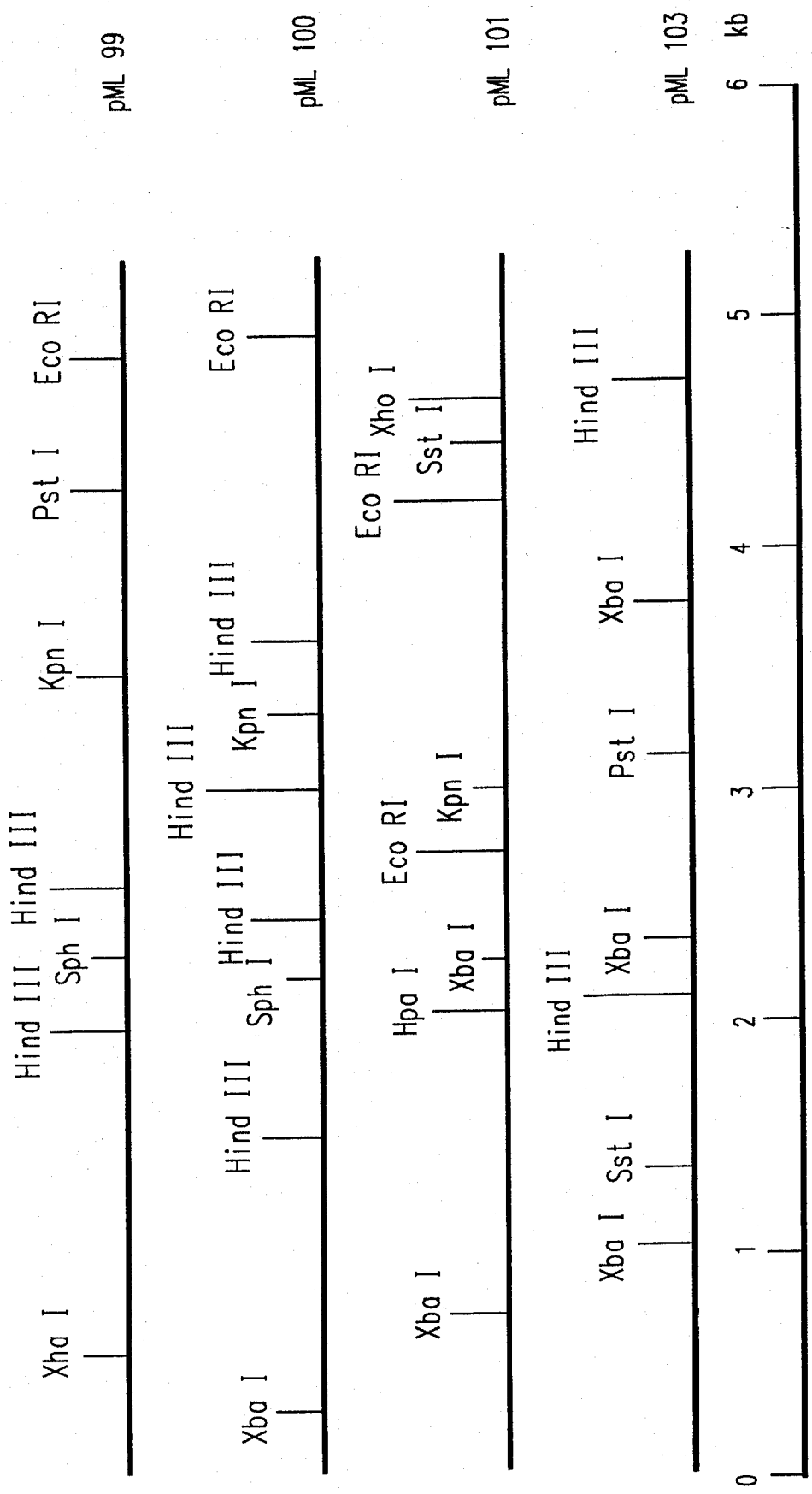
FIG. 1 shows restriction maps of four plasmid inserts recovered via selection for fenpropimorph resistance in *Saccharomyces cerevisiae* as described in Example 1. Selected restriction enzyme digestion sites are shown for each insert.

The *Saccharomyces cerevisiae* gene encoding sterol Δ14 reductase is cloned by selecting strains carrying sequences on a 2μ based vector for resistance to a morpholine fungicide. One of the plasmids so obtained is characterized and sequenced to obtain the primary structure of sterol Δ14 reductase.

By "morpholine fungicide" is meant any morpholine and structurally related piperidine compound having large ring N-substituents such as dodemorph, tridemorph, aldimorph, fenpropimorph, amorolfine, and fenpropidin which are employed as fungicides. Mixtures of morpholine fungicides may also be employed. Fenpropimorph is employed in one embodiment.

In morpholine screenings of *S. cerevisiae* strains carrying DNA sequences on a 2μ vector, plasmid inserts which produce morpholine resistance are recovered. For example, where fenpropimorph is the morpholine employed, four plasmids denoted pML99, pML100, pML101 and pML103 are recovered. Although fenpropimorph is reported to inhibit the enzymes sterol Δ14 reductase and Δ8–Δ7 isomerase, none of the inserts exhibit restriction maps resembling ERG2, the gene encoding Δ8–Δ7 isomerase. In addition, a 2μ plasmid carrying the ERG2 sequence does not produce fenpropimorph resistance.

Plasmid pML100 produces fenpropimorph resistance consistently when tested in a number of different genetic backgrounds. Tests with a panel of fungicides indicate that pML100 produces significant resistance only to the morpholine fungicides fenpropimorph, tridemorph, fenpropidin, and azasterol, compounds which have a shared site of action, the enzyme sterol Δ14 reductase. No increase in resistance is seen to a variety of other fungicides which are not sterol Δ14 reductase inhibitors, suggesting that pML100 encodes a function specific to sterol Δ14 reductase activity. Other investigators report that selection for fenpropidin or fenpropimorph resistance in other *S. cerevisiae* strains produce plasmids exhibiting properties similar to pML100 (Lorenz and Parks, cited above, and Marcireau, C., et al., cited above).

A chromosomal disruption of the sequence producing morpholine resistance results in ergosterol auxotrophy and the build-up of ignosterol, the sterol Δ14 reductase substrate. The DNA sequence which produces this activity is obtained (SEQ ID 1), which contains an open reading frame encoding an integral membrane protein, consistent with an enzyme catalyzing a reaction in the ergosterol biosynthesis pathway.

Thus, this invention provides a purified and isolated DNA sequence encoding *Saccharomyces cerevisiae* sterol Δ14 reductase. Because of the degeneracy of the genetic code, a variety of codon change combinations can be selected to form DNA that encodes sterol Δ14 reductase, so that any nucleotide deletion(s), addition(s), or point mutation(s) that result in a DNA encoding sterol Δ14 reductase are encompassed by this invention. Since certain codons are more efficient for polypeptide expression in certain types of organisms, the selection of gene alterations to yield DNA material that codes for the enzyme are preferably those that yield the most efficient expression in the type of organism which is to serve as the host of the recombinant vector. Altered codon selection may also depend upon vector construction considerations.

DNA which encodes Δ14 reductase may be natural, recombinant or synthetic. Thus, DNA of the invention may be isolated from yeast strains or constructed from oligonucleotides using conventional methods. Also encompassed are DNA sequences homologous or closely related to complementary DNA described herein, namely DNA sequences which hybridize, particularly under stringent conditions that result in pairing only between nucleic acid fragments that have a high frequency of complementary base sequences, to DNA encoding sterol Δ14 reductase particularly described herein, and RNA corresponding thereto. In addition to these sequences, DNA encompassed by this invention may contain additional sequences, depending upon vector construction sequences, that facilitate expression of the gene.

As described above, DNA encoding the sterol Δ14 reductase of this invention, or RNA corresponding thereto, are useful when introduced into a vector or plasmid, and the recombinant plasmid used to transform microbial host organisms such as *S. cerevisiae*. Other host cells such as *E. coli* may be employed in some embodiments. Especially useful in some embodiments are *S. cerevisiae* cells into which the gene has been introduced at high copy. This invention thus also provides novel, biologically functional RNA and DNA vectors and plasmids incorporating RNA and DNA sequences describing the reductase generated by standard means. Culture of host organisms stably transformed or transfected with such vectors or plasmids under conditions facilitative of large scale expression of the exogenous, vector-borne DNA or RNA sequences and isolation of the desired polypeptides from the growth medium, cellular lysates, or cellular membrane fractions are also provided.

The present invention provides for the total and/or partial manufacture of DNA sequences coding for sterol Δ14 reductase, and including such advantageous characteristics as incorporation of codons preferred for expression by selected hosts, provision of sites of cleavage by restriction by endonuclease enzymes, and provision of additional initial, terminal or intermediate DNA sequences which facilitate construction of readily expressed vectors.

DNA (and RNA) sequences of this invention code for all sequences useful in securing expression in procaryotic or eucaryotic host cells of polypeptide products having at least a part of the primary structural conformation, and one or more of the biological properties of sterol Δ14 reductase which are comprehended by: (a) the DNA sequence encoding sterol Δ14 reductase; (b) DNA sequences which hybridize to DNA sequences defined in (a) or fragments thereof; and (c) DNA sequences which, but for the degeneracy of the genetic code, would hybridize to the DNA sequences defined in (a) and (b) above. Specifically comprehended are genomic DNA sequences encoding allelic variant forms of the enzyme, and sequences encoding RNA, fragments thereof, and analogues wherein RNA or DNA sequences may incorporate codons facilitating transcription or RNA replication host cells.

Particularly useful are *S. cerevisiae* strains into which has been introduced a DNA sequence of this invention, particularly those having multiple copies of the gene. Such strains are useful in screens for sterol Δ14 reductase inhibition such as those described in copending U.S. application No. 08/107,348 filed concurrently with this application and incorporated in its entirety by reference. In an example screen, test samples are added to a yeast culture of a transformed strain such as a strain transformed with pML100, and to a corresponding control culture which does not have the introduced gene. Positive samples are identified after incubation by observation that growth inhibition in the culture having no introduced reductase gene exceeds growth in the corresponding culture having the introduced gene. In preferred embodiments, a known inhibitor of sterol Δ14 reductase is employed for comparison purposes in both cultures of the screen.

Other plasmids that produce morpholine resistance such as pML99, pML101, and pML103 described above are also useful in other screens for compounds that affect sterol biosynthesis, including screens for sterol Δ14 reductase inhibitors such as those described above. As set out more fully hereinafter, in initial genetic analyses, these plasmids show differences from pML100 in their interactions with ergosterol biosynthesis mutations. Hence, these plasmids are useful with screens such as those described above except that different yeast strains are employed. Alternatively, screening results with these plasmids can be used in combination with screening tests using pML100.

This invention also provides the polypeptide encoded by the sterol Δ14 reductase sequences of this invention, e.g., the polypeptide encoded by the open reading frame set out in SEQ ID NO 2. Correspondingly, the invention provides for manufacture (and development by site specific mutagenesis of cDNA and genomic DNA) of DNA sequences coding for microbial expression of sterol Δ14 reductase which differ from the forms specifically described herein in terms of identity or location of one or more amino acid residues (i.e., deletion and/or substitution analogues wherein one or more residues are added to a terminal or medial portion of the polypeptide), and which share the biological properties of the enzyme. In embodiments involving the microbial expression of polypeptides provided by the invention, isolation and purification employ standard methodology including, for example, preparative chromatographic separations and immunological separations, including monoclonal and/or polyclonal antibody preparations.

The sequence of pML100 exhibits partial homology to three other previously reported genes as follows (see FIG. 3): the chicken nuclear lamin B receptor (SEQ ID NO 3, Worman, H. J., et al., cited above; 101 out of 419 amino acids), the *S. cerevisiae* YGL022 sequence (SEQ ID NO 4, Chen, et al., cited above; 95 out of 473 amino acids), and the *Schizosaccharomyces pombe* sts1 gene (SEQ ID NO 5, Shimanuki, M., et al., cited above; 92 out of 453 amino acids). The phenotypes of strains carrying sts1 and YGL022 mutations are consistent with the hypothesis that these mutations produce lesions in erogsterol biosynthesis. The *S. pombe* sts1$^+$ gene and the *S. cerevisiae* YGL022 sequence have been reported to encode putative transport proteins which produce drug resistance by pumping compounds out of the cell. Mutations in these genes produce super-sensitivity to a wide variety of compounds. Drug super-sensitivity is also a phenotype associated with ergosterol biosynthesis mutations such as erg6 (Gaber, R. F., et al., *Mol. Cell. Biol.* 9: 3447–3456 (1989)), erg2 and erg3, presumably due to alterations in membrane function.

Physiological studies with an sts1 mutant strain and a YGL022 disruption strain more particularly described hereafter and complementation studies with YGL022 provide direct proof that sts1$^+$ and YGL022 encode a function in sterol biosynthesis identified as ERG4, sterol C-24(28) reductase, in *S. cerevisae*. Thus, the enzymes sterol Δ14 reductase and sterol C-24(28) reductase are related enzymes, with the former catalyzing the reduction of a double bond in the D ring and the latter catalyzing the reduction of a double bond in the side chain of the sterol.

The following examples are presented to further illustrate and explain the present invention and should not be taken as limiting in any regard. Fenpropimorph, fenpropidin and tridemorph are purchased from Crescent Chemical Company, Inc., Hauppauge, N.Y. Synthetic dextrose (SD) media contains 0.7% yeast nitrogen base without amino acids, 2% dextrose and 2% agar. Yeast extract, peptone and dextrose (YEPD) media contains 1% yeast extract, 2 % peptone, 2 % dextrose and 2 % agar.

EXAMPLE 1

This example describes the cloning and sequencing of the *Saccharomyces cerevisiae* gene encoding sterol Δ14 reductase. The gene is isolated and cloned by selecting strains carrying sequences on a 2μ based vector for resistance to the morpholine fungicide, fenpropimorph, to obtain a plasmid which is shown to carry the structural gene based upon the phenotype of gene disruption strains.

Isolation and characterization of morpholine resistance plasmids. Morpholine and structurally related piperidine fungicides reportedly inhibit sterol Δ14 reductase and sterol Δ8 to Δ7 isomerase (Baloch and Mercer, cited above). The growth of *S. cerevisiae* strain Y294, genotype MATα, leu2-3,112, ura3-52, his3A, trp1, Gal$^+$ (Brugge, J. S., et al., *Mol. Cell. Biol.* 7:2180–2187 (1987)), in SD medium supplemented with leucine, tryptophan, uracil and histidine is inhibited by 20 μg/ml of the morpholine fungicide fenpropimorph and 50 μg/ml of the morpholine fungicide tridemorph. Fenpropimorph is used for subsequent selection experiments because of its slightly greater potency.

When Y294 cells are plated onto 20 μg/ml of fenpropimorph in SD media supplemented with leucine, tryptophan, uracil and histidine, spontaneous mutants are recovered at the rate of ~1 per 2.5×10$^6$ plated cells. When a library of *S. cerevisiae* sequences in the multicopy vector YEp13 (Nasmyth, K. A., and Tatcheil, K., *Cell* 19: 753–764 (1980)) is introduced into strain Y294 and cells are plated on SD media supplemented with tryptophan, uracil, histidine and fenpropimorph, resistant colonies appeared at the rate of ~1 per 10$^4$, suggesting that resistance is produced by library plasmids in some of the colonies. Plasmids are cured from randomly selected resistant colonies by growing the cells in non-selective rich YEPD media and retesting for fenpropimorph resistance. In 13 strains, the plasmid-cured derivative shows sensitivity to 20 μg/ml fenpropimorph while the original plasmid carrying strain retested as fenpropimorph-resistant.

DNA is isolated from these 13 strains and plasmid DNA is recovered by *E. coli* transformation. Five different types of plasmid DNA are identified following an examination of restriction enzyme digestion patterns using standard methods (FIG. 1). Seven strains carry one plasmid type, pML99, which has an insert of approximately 5.5 kb. Two additional strains carry a second plasmid type, pML-100, which has an insert of approximately 5.6 kb. A third plasmid type, pML101, is found in two strains and carries an insert of approximately 5.5 kb. Two additional plasmid types are each recovered from a single strain and named pML102 (~7.5 kb insert) and pML103 (~5.1 kb insert). One representative plasmid of each type is selected and subjected to extensive restriction enzyme analysis, which indicates that the insert from plasmid pML101 is contained within the insert from pML102 so that a total of four unique sequences are recovered in this selection. Restriction enzyme digestion maps of the four different insert sequences are shown in FIG. 1.

A panel of fungicides representing a variety of chemical structures and mechanisms of action listed in Table 1 is tested by disk diffusion assay against strains carrying each of these plasmids in a YEp13 vector control. All five strains show similar levels of sensitivity to all of the tested compounds with the exception of the morpholines, fenpropidin, fenpropimorph and tridemorph, and azasterol. These compounds are less active on the strains carrying the four plasmids recovered by selection for fenpropimorph resistance. Consistent with agar dilution sensitivity results, fenpropimorph is more active by disk diffusion than tridemorph. These results suggest that the cloned sequences encode functions specific to the activity of morpholines and related compounds and do not carry genes which produce general fungicide resistance, e.g., by altering cell permeability.

TABLE 1

Fungicides Used For Plasmid Characterization

| Compound | Target |
| --- | --- |
| amphotericin B | plasma membrane (polyene) |
| cerulenin | fatty acid biosynthesis |
| haloprogin | respiration |
| ketoconazole | ergosterol biosynthesis (lanosterol 14α-demethylase) |
| miconazole | ergosterol biosynthesis (lanosterol 14α-demethylase) |
| dinaconazole | erogsterol biosynthesis (lanosterol 14α-demethylase) |
| econazole | erogsterol biosynthesis (lanosterol 14α-demethylase) |
| fepropimorph | erogsterol biosynthesis (sterol Δ14 reductase/Δ8–Δ7 isomerase) |
| tridemorph | erogsterol biosynthesis (sterol Δ14 reductase/Δ8–Δ7 isomerase) |
| azasterol | erogsterol biosynthesis (sterol Δ14 reductase) |
| tolnaftate | ergosterol biosynthesis (squalene monooxygenase) |
| U18666A | ergosterol biosynthesis (squalene cyclase) |
| cycloheximide | protein biosynthesis |
| polyoxin D | chitin biosynthesis (cell wall) |
| nikkomycin | chitin biosynthesis (cell wall) |
| nocodazole | microtubule assembly |
| benomyl | microtubule assembly |
| maneb | multi-target |
| metalaxyl | rRNA biosynthesis |
| vinclozoline | lipid peroxidation |
| kanamycin | mitochondria |
| tunicamycin | glycoprotein biosynthesis |
| carboxin | succinate dehydrogenase |
| antimycin | respiration |
| 5-fluorocytosine | nucleotide metabolism |
| cyanobutarate | microtubule assembly (hericide) |
| glyphosate | aromatic amino acid biosynthesis (herbicide) |
| phosphinothricin | glutamine biosynthesis (herbicide) |
| aminotriazole | histidine biosynthesis (herbicide) |
| sulfometuron methyl | branched chain amino acid biosynthesis (herbicide) |
| pendimethalin | microtubule assembly (herbicide) |

The library employed for the selection is prepared using DNA isolated from strain AB320 (genotype HO, ade2-1, lys2-1, trp5-2, leu2-1, can1-100, ura3-1 and/or ura1-1, met4-1, Nasmyth and Tatcheil, cited above). When tested, strain AB320 is found to be slightly more sensitive to fenpropimorph than strain Y294, suggesting that the cloned sequences are likely to be producing resistance as the result of gene dosage effects.

Morpholine resistance in strains transformed with multicopy ERG2 (sterol Δ8–Δ7 isomerase) plasmids. One gene that would be expected to produce morpholine resistance at high copy is ERG2, which encodes a reported morpholine target, Δ8–Δ7 isomerase. This gene was recently cloned by the complementation of a polyene resistance mutation (Ashman, cited above). The published ERG2 restriction map is different from the restriction maps of the four sequences recovered by morpholine resistance selection. Since it is possible that the ERG2 sequence is missed in the morpholine resistance screen, this gene is introduced into S. cerevisiae strain Y294 on the 2μ based plasmid, pML104, constructed by subcloning the ERG2 gene on a 2.1 kb HindIII fragment from plasmid PIU406 (Ashman, et al., cited above) into the HindIII site of plasmid YEp351. This strain shows no increase in fenpropimorph resistance relative to YEp351-transformed control strain. Plasmid pML104 does, however, produce nystatin sensitivity when introduced into the erg2 mutant strain WAO (Ashman, et al., cited above), demonstrating that plasmid pML104 carries a functional ERG2 gene. Sterol Δ8–Δ7 isomerase may not over-express when present on a 2μ based, multicopy plasmid, or the enzyme may not be a morpholine target in S. cerevisiae.

Characterization of fenpropimorph resistance plasmid pML100. The four fenpropimorph-resistance plasmids pML99, pML100, pML101, and pML103 are transformed into three ergosterol pathway mutant strains, erg2 (denoted WAO, genotype MATa, his7-2, leu2-3, 112, ura3-52, erg2-3, Ashman, et al., cited above); erg3 (denoted XML39-1d, genotype MATa, leu2-3,112, erg3-2); and erg6 (denoted XML40-1c, genotype MATα, leu2-3,112, gal2, erg6-5). Morpholine sensitivity is determined by disk diffusion assay on appropriately supplemented SD medium using tridemorph and fenpropimorph. A zone size difference of greater than 3 mm performed in duplicate is recorded as resistance. The ergosterol pathway mutant strains vary in absolute level of morpholine sensitivity, and all resistance and sensitivity determinations are reported relative to vector (YEp-13)-transformed control strains. The results are tabulated in Table 2. Only plasmid pML100 transformants are consistently fenpropimorph-resistant in all genetic backgrounds.

TABLE 2

Plasmid Phenotype in Ergosterol Pathway Mutant Strains

| Strain | Ergosterol Genotype | Plasmid | Morpholine Resistance |
| --- | --- | --- | --- |
| Y294 | ERG+ | YEp13 | − |
| Y294 | ERG+ | pML99 | + |
| Y294 | ERG+ | pML100 | + |
| Y294 | ERG+ | pML101 | + |
| Y294 | ERG+ | pML103 | + |
| WAO | erg2 | YEp13 | − |
| WAO | erg2 | pML99 | − |
| WAO | erg2 | pML100 | + |
| WAO | erg2 | pML101 | − |
| WAO | erg2 | pML103 | − |
| XML39-1d | erg3 | YEp13 | − |
| XML39-1d | erg3 | pML99 | + |
| XML39-1d | erg3 | pML100 | + |
| XML39-1d | erg3 | pML101 | − |
| XML39-1d | erg3 | pML103 | +/−* |
| XML40-1c | erg6 | YEp13 | − |
| XML40-1c | erg6 | pML99 | + |
| XML40-1c | erg6 | pML100 | + |
| XML40-1c | erg6 | pML101 | − |

TABLE 2-continued

Plasmid Phenotype in Ergosterol Pathway Mutant Strains

| Strain | Ergosterol Genotype | Plasmid | Morpholine Resistance |
|---|---|---|---|
| XML40-1c | erg6 | pML103 | +/−* |

*Resistance was observed with fenpropimorph but not tridemorph.

Resistance is also seen with other morpholine antifungals (tridemorph and fenpropidin) and azasterol, all of which are reported to be inhibitors of sterol Δ14 reductase. However, no increase is seen to a variety of other fungicides which are not sterol Δ14 reductase inhibitors. Since resistance occurs only to sterol Δ14 reductase inhibitors and is seen for such inhibitors from two different chemical classes, it is likely that pML100 encodes a function specific to sterol Δ14 reductase activity.

Figure 2:
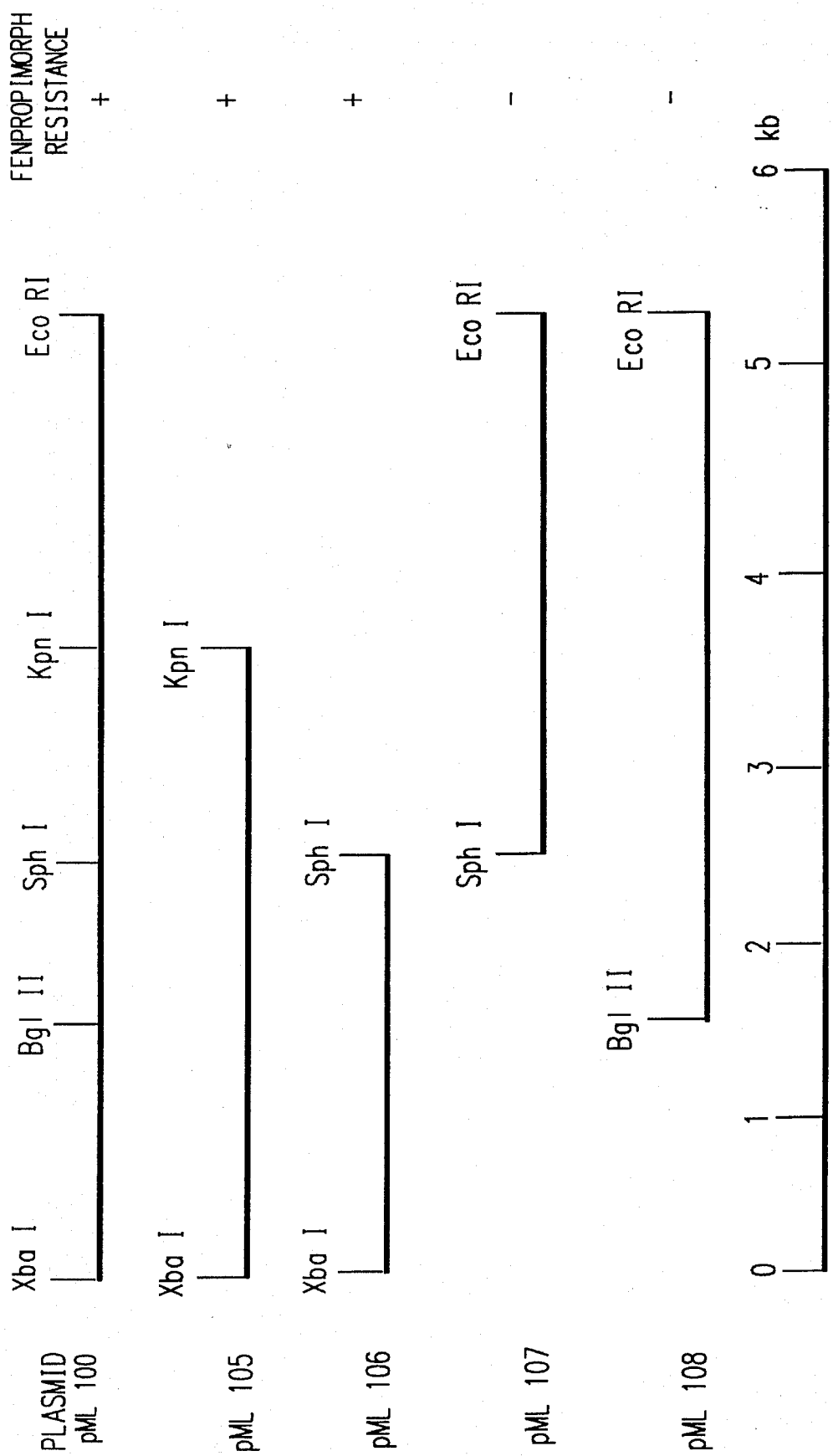
FIG. 2 shows fenpropimorph resistance of subclones of pML100, a plasmid containing the cloned sterol Δ14 reductase gene.

Subclones of the pML100 insert are prepared in the yeast shuttle vector YEp352, transformed into yeast strain Y294, and tested for fenpropimorph resistance. As shown in FIG. 2, the fenpropimorph resistance region is limited to a 2.5 kb SphI/XbaI fragment located near one side of the insert/vector border.

Plasmid pML106, which contains this fragment in vector YEp352, is cleaved with BglII, which cuts once at a site near the middle of the SphI/XbaI fragment. A 3.0 kb BglII fragment containing the S. cerevisiae LEU2 gene is isolated from plasmid YEp13 and ligated into this BglII cite, producing plasmid pML108. The disrupted 5.5 kb SphI/XbaI fragment containing the LEU2 gene is isolated from plasmid pML108 and used to transform S. cerevisiae strain YPH501 to leucine prototrophy. Transformants in which the 5.5 kb SphI/XbaI fragment replaced the 2.5 kb SphI/XbaI fragment in one chromosomal homologue are identified by Southern analysis.

Tetrads from one such transformant (strain YPH501-2-1) are dissected and the spores germinated under anaerobic conditions on YEPD medium supplemented with Tween® 80 (500 μg/ml) and ergosterol (20 μg/ml). Strain YPH501-2-1 shows low (approximately 50%) spore viability, and no tetrads are recovered. This is found to be a property of strain YPH501 which showed a similar low level of spore viability when spores from the host strain are germinated anaerobically. By random spore analysis, 15 of 32 segregants are both Leu⁺ and obligate anaerobes, suggesting that the disruption has produced a genetic lesion in sterol biosynthesis. (The remaining 17 segregants are Leu⁻ and grow aerobically.)

One such obligate anaerobe segregant, denoted YPH501-2-1-3C, is analyzed for sterol content. The strain is grown anaerobically on YEPD medium containing ergosterol (5 μg/ml) to facilitate sterol uptake. After one day, the cells are harvested, washed in saline, resuspended in YEPD medium with no added sterol and grown for an additional 2 days to deplete cellular sterol. After 3 days, sterols are extracted from stationary phase yeast cells into n-heptane and analyzed by ultraviolet (UV) between 200 and 300 nm, gas chromatography (GC) and gas chromatography/mass spectrometry (GC-MS). GC-MC analyses are performed on a Hewlett Packard (HP) 5980 instrument using a 30 meter× 0.25 mmHP-5 column with a 25 micron film thickness. The column temperature is programmed from 280° C. to 300° C. with the initial temperature maintained for 2 minutes and increased at 3° C./minute. The final temperature is held for 6 minutes. The mass spectrometer is operated in the electron impact ionization mode at 70 eV. High pressure liquid chromatography (HPLC) analyses are performed using a reverse phase column (2.1×100 mm) packed with 5 micron spherical C18 bonded silica. Sterol samples are dissolved in a methanol:ethyl acetate (1:1) mixture and eluted from HPLC with 95% acetonitrile in water at 1 ml/minute. The detection wavelength is 270 nm.

UV analysis demonstrates a 250 nm broad peak indicative of a sterol containing a conjugated double bond system involving C-8(9) and C-14(15). GC analyses indicate a major peak with the relative retention time of 1.30 consistent with ignosterol (ergosta-8,14-dien-3β-ol, molecular weight 398), the sterol Δ14 reductase substrate. GC-MS analysis confirms that the major sterol accumulating in this disrupted strain is ignosterol. Small amounts of lanosterol, approximately 5%, are also observed, consistent with a block in the sterol pathway downstream of lanosterol and affecting the reduction of the C-14 double bond. The accumulation of ignosterol indicates a genetic lesion in sterol Δ14 reductase activity.

DNA sequence analysis of plasmid pML100. DNA sequences are performed using an Applied Biosystems automatic DNA sequencer from Applied Biosystems, Inc., Foster City, Calif. 94404, following the manufacturer's directions. Dye primers and dye terminators are used as appropriate for the insert to be sequenced. Oligonucleotides used for sequencing with dye terminators are synthesized using an Applied Biosystems oligonucleotide synthesizer according to the manufacturer's directions.

The DNA sequence of the 2.5 kb SphI/XbaI fragment of plasmid pML100 is set out in the Sequence Listing section hereinafter as SEQ ID NO 1. An open reading frame of 1314 base pairs is identified starting at an ATG codon at position 419 within the sequence. No other open reading frame of significant size is present within this fragment. Upstream of this ATG codon is an AT-rich sequence (66%), typical of many functionally expressed S. cerevisiae genes. This open reading frame encodes a 438 amino acid, 50.5 kilo-dalton basic (pI=9.2), presumptive integral membrane protein which, based upon hydropathy analysis using a computer program that progressively evaluates the hydrophilicity and hydrophobicity of a protein along its amino acid sequence (Kyte, J., and Doolittle, R. F., J. Mol. Biol. 157: 105–132 (1982)), contains 8 or 9 putative transmembrane domains.

EXAMPLE 2

The open reading frame of the plasmid pML100 DNA sequence of Example 1 is compared to other sequences in this example.

Figure 3B:
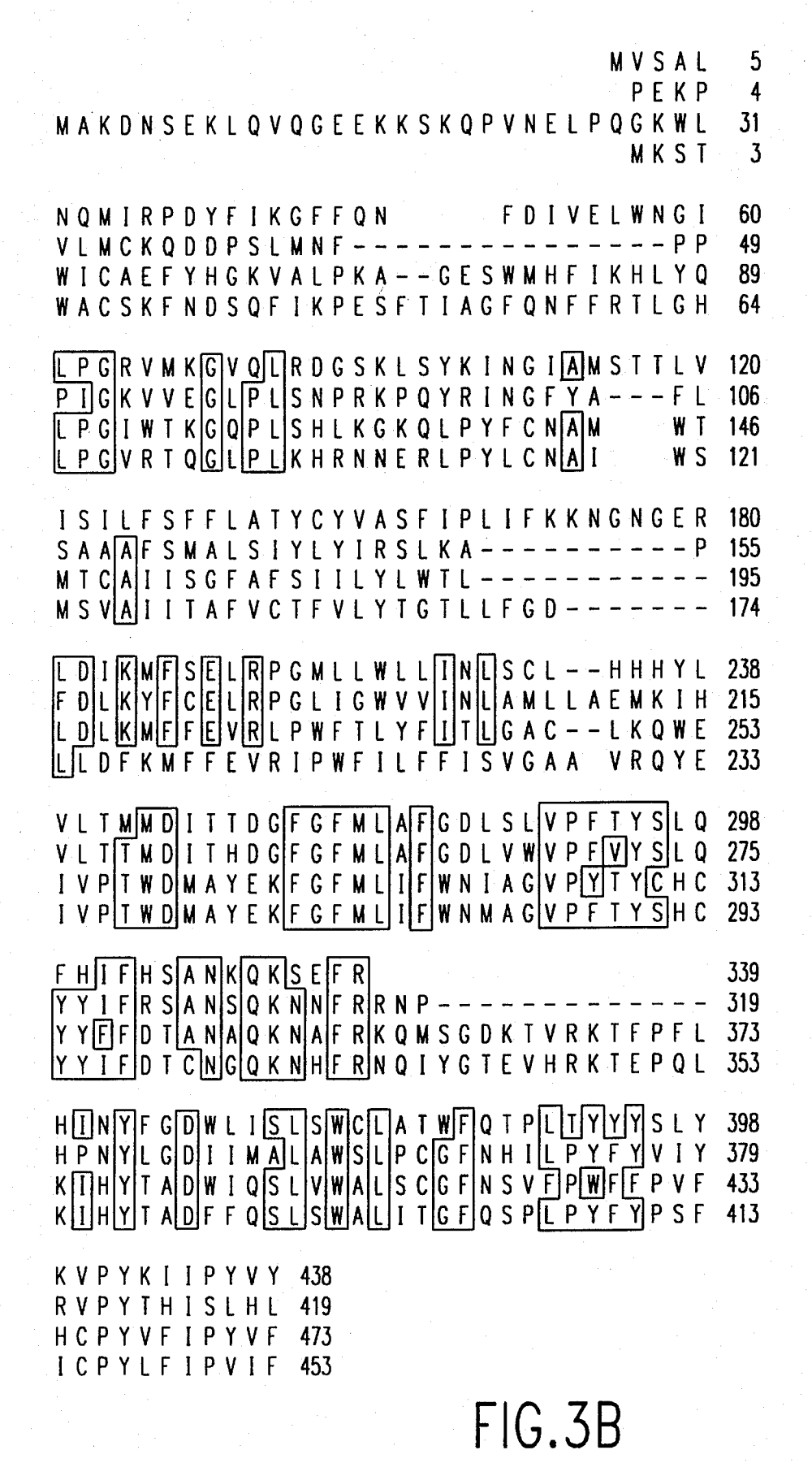

The sequence is compared with sequences deposited in the Genbank® DNA sequence data base. Three sequences show partial homology: the chicken nuclear lamin B receptor (SEQ ID NO 3, Worman, H. J., et al., cited above; 101 out of 419 amino acids), the S. cerevisiae YGL022 sequence (SEQ ID NO 4, Chen, et al., cited above; 95 out of 473 amino acids) and the S. pombe sts1 gene (SEQ ID NO 5, Shimanuki, M., et al., cited above; 92 out of 453 amino acids). A comparison of the amino acid sequences of the three yeast genes is shown in FIG. 3. A certain amount of sequence similarity is seen along the entire length of the three sequences and is particularly pronounced at the carboxy termini of these polypeptides.

EXAMPLE 3

The physiological characteristics of mutant phenotypes Schizosaccharomyces pombe sts1 and Saccharomyces cerevisiae YGL022 found to be somewhat homologous to the pML100 sequence as described in Example 2 are characterized in this example.

S. pombe strains HM123 and JY6(sts1+) and 111-1A (sts1) are obtained and analyzed for their sterol profiles. UV, GC-MC and HPLC analyses are carried out as described in Example 1 above; proton nuclear magnetic resonance (NMR) analysis on samples dissolved in $d_6$-acetone is obtained on a Brunker AMX300 MHz spectrometer, Brunker Instruments, Inc., Billerica, Mass. 01821. As set out in the data summarized in Table 3 below, while the wild-type strains accumulate ergosterol and small amounts of lanosterol and perhaps 24-methylene-dihydrolanosterol (molecular weight 440), the mutant strain acccumulated principally the tetraene, ergosta-5,7,22,24(28)-tetraen-3-β-ol. The conversion of the tetraene to ergosterol is considered to be the last step in ergosterol biosynthesis and the gene encoding this enzymatic step has been designated ERG4 in S. cerevisiae as discussed above. Whereas ergosterol gives absorption maxima at 262, 271, 282 and 293 nm, the precursor 24(28)-ergosterol gives absorption maxima at 232 nm reflecting the presence of a conjugated double bond system in the sterol side chain. The identity of the tetraene is confirmed by GC-MS and NMR.

GC-MS analysis shows a molecular ion at M/Z 394, 2 atomic mass units less than ergosterol. An ion is present at M/Z 123 which has no counterpart in the spectrum of ergosterol. This ion is proposed to represent the side chain fragment $C_9H_{15}$ indicating the presence of two unsaturations. Consistent with the UV and GC-MS analyses, the structure of the conjugated side chain is substantiated by proton NMR signals indicative of the exomethylene protons (chemical shift 4.71 and 4.73, broad singlets) and signals for H22 (chemical shift 5.52, $J_{21,22}$=8.8 Hz, $J_{22,23}$=15.8 Hz) and H23 (chemical shift 5.87, $J_{23,22}$=15.8 Hz). The chemical shift values for the latter two protons are considerably downfield from their position in ergosterol, which has a chemical shift of about 5.25, reflecting the deshielding effects of the conjugation with the C-24(28) double bond.

This provides further evidence that an additional double bond is present in the sterol side chain.

Upon transformation of strain TP111-1A with a plasmid pST2SC which contains the wild-type C-24(28) reductase gene, an ergosterol profile is observed. However, when selection pressure is removed such that the plasmid is lost, the tetraene profile is restored, indicating that ergosterol synthesis requires the presence of the plasmid containing the wild-type gene (Table 3). Thus, sts1+ appears to encode a protein in the ergosterol biosynthesis pathway.

YGL022 is then characterized. A leaky, S. cerevisiae erg4 mutant strain (Molzahn, S. W., and Woods, R. A., J. Gen Microbiol. 72: 339–348 (1972)) is subjected to sterol analysis as described above. Approximately 35% ergosterol and 60% ergosta-5,7,22,24(28)-tetraen-3β-ol accumulates. When this strain is transformed with plasmid pA-B6.5 carrying the YGL022 sequence (Balzi, E., et al., J. Biol. Chem. 262: 16871–16879 (1987)) and retested, mostly ergosterol is detected (Table 3).

To confirm these findings, the open reading frame in YGL022 (in plasmid pA-B6.5) is disrupted by deleting an approximately 0.6 kb SmaI/AccI fragment internal to the open reading frame and replacing this with an approximately 2.2 kb HpaI fragment carrying the LEU2 gene (in a gene disruption construction similar to that described by Chen, et al., cited above). This sequence is released from the plasmid by XhoI and BamHI digestion, and the linear sequence is transformed into a diploid strain XML25 which is then sporulated. Integration of the construction into the YGL022 sequence is confirmed by Southern analysis.

Forty-seven tetrads are studied and all show 2:2 segration for leucine prototrophy. Leucine auxotrophic segregants are all wild-type for drug sensitivity while leucine prototrophic segregants show increased sensitivity to cycloheximide. One tetrad is analyzed for ergosterol content. The leucine auxotrophic segregants synthesize ergosterol while the leucine prototrophic segretants do not synthesize ergosterol and accumulate ergosta-5,7,22,24(28)-tetraen-3β-ol (Table 3). This indicates that the YGL022 sequence is required for sterol C-24(28) reductase activity (ERG4) in S. cerevisiae.

TABLE 3

Sterol Accumulation Patterns in Wild-Type and erg4 Yeast Strains

| | | | % Sterol Content | | |
|---|---|---|---|---|---|
| Species | Strain | Genotype | Ergosterol | 24(28) Tetraene | Other Sterol |
| S. pombe | HM123 | erg4+ | 86 | 0 | 4 |
| S. pombe | JY-6 | erg4+ | 94 | 0 | 6 |
| S. pombe | TP111-1A | erg4 | 0 | 94 | 6 |
| S. pombe | TP111-1A(pST2Sc) | erg4+ | 100 | 0 | 0 |
| S. pombe | TP111-1A cured | erg4 | 0 | 100 | 0 |
| S. cerevisiae | erg4-1A | erg4+/– | 29 | 68 | 3 |
| S. cerevisiae | erg4-1A(pA-B6.5) | ERG4 | 83 | 5 | 12 |
| S. cerevisiae | erg4-1A cured | erg+/– | 37 | 57 | 6 |
| S. cerevisiae | XML25-2-1A | erg4Δ | 0 | 97 | 3 |
| S. cerevisiae | XML25-2-1B | ERG4 | 91 | 0 | 9 |
| S. cerevisiae | XML25-2-1C | erg4Δ | 0 | 98 | 2 |
| S. cerevisiae | XML25-2-1D | ERG4 | 88 | 0 | 12 |

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

---

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 2528 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Saccharomyces cerevisiae ( i x ) FEATURE:
        ( A ) NAME/KEY: CDS
        ( B ) LOCATION: 419..1732

( x i ) SEQUENCE DESCRIPTION: SEQ ID NO:1:

```
ATATATATAT   ACCTCTTGCC   AGCAACAGGC   CAGTTATAAG   TTAAAATTAA   TATGTGACGC         60

ACTTCTGAAA   CAGTATTGAA   ACAGTATTGA   AACATATGTA   TTACCCGGAC   TCTGCATGCT        120

CTGTCGTTCA   TTTTATTTTC   ACCTAAACGA   AAATCCCGTG   AAAAAAATTT   ATATCGCCTT        180

TCGCTCTTTT   GTATGTAGGC   ATCATCGGAA   ATTTGCATTG   TGTGAAGGTT   GTGCATATAA        240

AGGGTTTTGC   ATAACGGACG   TTTTTCACGT   ACTCCGTCTG   AGCATCAAGT   GAGGCTTGAG        300

TTTACGTTTG   TTTTTAATAA   TCAGTTTTCA   TTCTACTATT   TTCTTGCGCA   ATTGCTTATC        360

AGATAGACCT   TGTAAACAGC   ATAGGAGTAA   AGACAAATTC   GGTGTAGAGA   ATAAAAGG          418

ATG   GTA   TCA   GCT   TTG   AAT   CCC   AGA   ACT   ACA   GAG   TTT   GAA   TTT   GGT   GGG        466
Met   Val   Ser   Ala   Leu   Asn   Pro   Arg   Thr   Thr   Glu   Phe   Glu   Phe   Gly   Gly
 1                      5                           10                          15

CTG   ATT   GGT   GCC   TTA   GGC   ATC   AGC   ATA   GGG   CTG   CCT   GTT   TTC   ACT   ATC        514
Leu   Ile   Gly   Ala   Leu   Gly   Ile   Ser   Ile   Gly   Leu   Pro   Val   Phe   Thr   Ile
                 20                          25                          30

ATC   TTG   AAT   CAA   ATG   ATA   AGG   CCC   GAT   TAT   TTT   ATT   AAG   GGA   TTT   TTC        562
Ile   Leu   Asn   Gln   Met   Ile   Arg   Pro   Asp   Tyr   Phe   Ile   Lys   Gly   Phe   Phe
         35                          40                          45

CAG   AAT   TTC   GAT   ATA   GTT   GAG   CTT   TGG   AAC   GGT   ATC   AAG   CCA   TTG   CGC        610
Gln   Asn   Phe   Asp   Ile   Val   Glu   Leu   Trp   Asn   Gly   Ile   Lys   Pro   Leu   Arg
     50                          55                          60

TAC   TAT   CTG   GGC   AAT   CGT   GAA   TTA   TGG   ACT   GTC   TAT   TGC   CTG   TGG   TAT        658
Tyr   Tyr   Leu   Gly   Asn   Arg   Glu   Leu   Trp   Thr   Val   Tyr   Cys   Leu   Trp   Tyr
 65                      70                          75                          80

GGA   ATA   CTG   GCA   GTT   TTG   GAC   GTC   ATT   TTA   CCG   GGC   AGA   GTC   ATG   AAG        706
Gly   Ile   Leu   Ala   Val   Leu   Asp   Val   Ile   Leu   Pro   Gly   Arg   Val   Met   Lys
                 85                          90                          95

GGT   GTT   CAG   TTA   AGG   GAT   GGT   TCG   AAG   CTT   TCG   TAT   AAG   ATC   AAT   GGA        754
Gly   Val   Gln   Leu   Arg   Asp   Gly   Ser   Lys   Leu   Ser   Tyr   Lys   Ile   Asn   Gly
                 100                         105                         110

ATT   GCC   ATG   TCT   ACA   ACT   TTG   GTC   TTA   GTT   TTG   GCT   ATC   AGA   TGG   AAA        802
Ile   Ala   Met   Ser   Thr   Thr   Leu   Val   Leu   Val   Leu   Ala   Ile   Arg   Trp   Lys
                 115                         120                         125
```

```
TTG ACT GAT GGA CAA TTG CCT GAA TTG CAA TAT CTG TAT GAA AAT CAC      850
Leu Thr Asp Gly Gln Leu Pro Glu Leu Gln Tyr Leu Tyr Glu Asn His
    130                 135                 140

GTT AGT TTA TGC ATA ATA TCT ATT TTG TTT TCG TTC TTT TTG GCG ACG      898
Val Ser Leu Cys Ile Ile Ser Ile Leu Phe Ser Phe Phe Leu Ala Thr
145                 150                 155                 160

TAC TGC TAT GTT GCC AGC TTC ATA CCA TTG ATC TTC AAG AAA AAT GGT      946
Tyr Cys Tyr Val Ala Ser Phe Ile Pro Leu Ile Phe Lys Lys Asn Gly
                165                 170                 175

AAT GGC AAA AGG GAA AAG ATC TTA GCA CTA GGT GGA AAT TCA GGA AAC      994
Asn Gly Lys Arg Glu Lys Ile Leu Ala Leu Gly Gly Asn Ser Gly Asn
            180                 185                 190

ATC ATT TAC GAT TGG TTT ATT GGT AGA GAA CTG AAC CCT CGT CTC GGC     1042
Ile Ile Tyr Asp Trp Phe Ile Gly Arg Glu Leu Asn Pro Arg Leu Gly
        195                 200                 205

CCA TTA GAT ATC AAG ATG TTT TCA GAG TTG AGA CCC GGC ATG TTG TTA     1090
Pro Leu Asp Ile Lys Met Phe Ser Glu Leu Arg Pro Gly Met Leu Leu
    210                 215                 220

TGG TTA CTG ATC AAT CTT TCC TGT CTG CAT CAC CAT TAC CTG AAG ACT     1138
Trp Leu Leu Ile Asn Leu Ser Cys Leu His His His Tyr Leu Lys Thr
225                 230                 235                 240

GGT AAA ATC AAC GAT GCA TTG GTC TTG GTT AAT TTC TCG CAA GGA TTT     1186
Gly Lys Ile Asn Asp Ala Leu Val Leu Val Asn Phe Ser Gln Gly Phe
                245                 250                 255

TAC ATT TTC GAT GGA GTA CTA AAC GAG GAA GGT GTA TTA ACC ATG ATG     1234
Tyr Ile Phe Asp Gly Val Leu Asn Glu Glu Gly Val Leu Thr Met Met
            260                 265                 270

GAT ATC ACT ACA GAT GGG TTT GGT TTC ATG CTA GCG TTT GGT GAC TTA     1282
Asp Ile Thr Thr Asp Gly Phe Gly Phe Met Leu Ala Phe Gly Asp Leu
        275                 280                 285

AGT TTA GTT CCA TTC ACC TAC TCA TTA CAA GCG CGT TAC TTG AGT GTT     1330
Ser Leu Val Pro Phe Thr Tyr Ser Leu Gln Ala Arg Tyr Leu Ser Val
    290                 295                 300

TCC CCT GTG GAA TTG GGA TGG GTG AAA GTT GTC GGT ATA TTA GCC ATA     1378
Ser Pro Val Glu Leu Gly Trp Val Lys Val Val Gly Ile Leu Ala Ile
305                 310                 315                 320

ATG TTT TTG GGT TTC CAC ATC TTC CAC TCG GCA AAT AAG CAA AAA TCT     1426
Met Phe Leu Gly Phe His Ile Phe His Ser Ala Asn Lys Gln Lys Ser
                325                 330                 335

GAG TTT AGA CAA GGT AAA TTA GAA AAT CTA AAA AGT ATT CAG ACA AAG     1474
Glu Phe Arg Gln Gly Lys Leu Glu Asn Leu Lys Ser Ile Gln Thr Lys
            340                 345                 350

CGT GGT ACA AAG TTA TTA TGT GAC GGG TGG TGG GCT AAA TCA CAG CAT     1522
Arg Gly Thr Lys Leu Leu Cys Asp Gly Trp Trp Ala Lys Ser Gln His
        355                 360                 365

ATC AAT TAC TTT GGC GAT TGG CTG ATT TCA TTA AGT TGG TGT TTG GCC     1570
Ile Asn Tyr Phe Gly Asp Trp Leu Ile Ser Leu Ser Trp Cys Leu Ala
    370                 375                 380

ACC TGG TTC CAA ACT CCC TTG ACA TAT TAC TAC TCG TTG TAC TTC GCC     1618
Thr Trp Phe Gln Thr Pro Leu Thr Tyr Tyr Tyr Ser Leu Tyr Phe Ala
385                 390                 395                 400

ACG TTG TTA TTA CAC CGT CAA CAA CGT GAT GAG CAC AAG TGC CGC CTG     1666
Thr Leu Leu Leu His Arg Gln Gln Arg Asp Glu His Lys Cys Arg Leu
                405                 410                 415

AAA TAT GGC GAA AAT TGG GAA GAA TAC GAA AGA AAA GTT CCT TAC AAG     1714
Lys Tyr Gly Glu Asn Trp Glu Glu Tyr Glu Arg Lys Val Pro Tyr Lys
            420                 425                 430

ATC ATT CCA TAT GTT TAT TAAGTTTTTC TACCACTGCT ATTTTCTTCA            1762
Ile Ile Pro Tyr Val Tyr
        435
```

```
TTATCTATGT ATGTGTGTAT ACATGTTATG TATTGGGTGA GTATGAGGAA GAAGAAGAAT      1822

AACAATTGAA AACGCTGGAA AAATTAAAAG GGGTGGCGGT CTATCTATGC AACGCTCCCC      1882

TTTTCGTTAC ATGAACACAT CAAACTTGTA TATCCTTTGA GTGTTCTTTA ATCAAGTCAT      1942

CTTGGTATTT TAGTAGCGTT TCCACTACTT TAGGGACAAA TTCAGACCTA ACCAATCCAT      2002

CAAAAGCATC AAACCCTTGC GACAAAATCG GAATATCAGA CTCGCCATGC ATAAACTCTG      2062

GAATTTCTAG TTTCCCGTCC GCAAGTATGC CGTCATCATC CTCGTCGTCC TTATTAGTAT      2122

CCAAATTTGT CACTTTGACG TTCATCGACA ACTGTAAGTC AAAGTAGCAA ATCGCCTTGC      2182

CCTTCCTTTG AGATACGTTG GAGTCACCGG TGATGCTACT CACCTGGGTT AACTCAATTT      2242

TGCTCTTCCC ATCAGAGGAA ACAGTGGACA AACTCGTTAA TTTACCGTTC AAGTAGTCCT      2302

TAGACCAAGG TAAGGTGTTT TTATCCACCC AATGCCAGTT ATTTGGATTC AAGACAACCA      2362

TATTTATCG TAAATGTGTT GTAACTTTCC GATCGTTTCA AACTTAGTA GTAGTTTGAT        2422

GATTTGTCC AAAAAGTATT TGCTTAAATT TCAGCTTTTT TCTTCTTCAT ATGTATTTCT       2482

TTTTTTCCTC GCTTTCTCTG CCCACTTTTT TCTTCTGTCT TCTAGA                     2528
```

(2) INFORMATION FOR SEQ ID NO:2:

(i) SEQUENCE CHARACTERISTICS:
        (A) LENGTH: 438 amino acids
        (B) TYPE: amino acid
        (D) TOPOLOGY: linear (ii) MOLECULE TYPE: protein (xi) SEQUENCE DESCRIPTION: SEQ ID NO:2:

```
Met Val Ser Ala Leu Asn Pro Arg Thr Thr Glu Phe Glu Phe Gly Gly
 1               5                  10                  15

Leu Ile Gly Ala Leu Gly Ile Ser Ile Gly Leu Pro Val Phe Thr Ile
                20                  25                  30

Ile Leu Asn Gln Met Ile Arg Pro Asp Tyr Phe Ile Lys Gly Phe Phe
            35                  40                  45

Gln Asn Phe Asp Ile Val Glu Leu Trp Asn Gly Ile Lys Pro Leu Arg
        50                  55                  60

Tyr Tyr Leu Gly Asn Arg Glu Leu Trp Thr Val Tyr Cys Leu Trp Tyr
 65                  70                  75                  80

Gly Ile Leu Ala Val Leu Asp Val Ile Leu Pro Gly Arg Val Met Lys
                85                  90                  95

Gly Val Gln Leu Arg Asp Gly Ser Lys Leu Ser Tyr Lys Ile Asn Gly
               100                 105                 110

Ile Ala Met Ser Thr Thr Leu Val Leu Val Leu Ala Ile Arg Trp Lys
            115                 120                 125

Leu Thr Asp Gly Gln Leu Pro Glu Leu Gln Tyr Leu Tyr Glu Asn His
        130                 135                 140

Val Ser Leu Cys Ile Ile Ser Ile Leu Phe Ser Phe Phe Leu Ala Thr
145                 150                 155                 160

Tyr Cys Tyr Val Ala Ser Phe Ile Pro Leu Ile Phe Lys Lys Asn Gly
                165                 170                 175

Asn Gly Lys Arg Glu Lys Ile Leu Ala Leu Gly Gly Asn Ser Gly Asn
            180                 185                 190

Ile Ile Tyr Asp Trp Phe Ile Gly Arg Glu Leu Asn Pro Arg Leu Gly
        195                 200                 205

Pro Leu Asp Ile Lys Met Phe Ser Glu Leu Arg Pro Gly Met Leu Leu
        210                 215                 220
```

| | | | | | | | | | | | | | | | |
|---|---|---|---|---|---|---|---|---|---|---|---|---|---|---|---|
| Trp<br>225 | Leu | Leu | Ile | Asn<br>230 | Leu | Ser | Cys | Leu | His<br>235 | His | His | Tyr | Leu | Lys | Thr<br>240 |
| Gly | Lys | Ile | Asn | Asp<br>245 | Ala | Leu | Val | Leu<br>250 | Val | Asn | Phe | Ser | Gln<br>255 | Gly | Phe |
| Tyr | Ile | Phe | Asp<br>260 | Gly | Val | Leu | Asn | Glu<br>265 | Glu | Gly | Val | Leu | Thr<br>270 | Met | Met |
| Asp | Ile | Thr<br>275 | Thr | Asp | Gly | Phe | Gly<br>280 | Phe | Met | Leu | Ala | Phe<br>285 | Gly | Asp | Leu |
| Ser | Leu<br>290 | Val | Pro | Phe | Thr | Tyr<br>295 | Ser | Leu | Gln | Ala | Arg<br>300 | Tyr | Leu | Ser | Val |
| Ser<br>305 | Pro | Val | Glu | Leu | Gly<br>310 | Trp | Val | Lys | Val | Val<br>315 | Gly | Ile | Leu | Ala | Ile<br>320 |
| Met | Phe | Leu | Gly | Phe<br>325 | His | Ile | Phe | His | Ser<br>330 | Ala | Asn | Lys | Gln | Lys<br>335 | Ser |
| Glu | Phe | Arg | Gln<br>340 | Gly | Lys | Leu | Glu | Asn<br>345 | Leu | Lys | Ser | Ile | Gln<br>350 | Thr | Lys |
| Arg | Gly | Thr<br>355 | Lys | Leu | Leu | Cys | Asp<br>360 | Gly | Trp | Trp | Ala | Lys<br>365 | Ser | Gln | His |
| Ile | Asn<br>370 | Tyr | Phe | Gly | Asp | Trp<br>375 | Leu | Ile | Ser | Leu | Ser<br>380 | Trp | Cys | Leu | Ala |
| Thr<br>385 | Trp | Phe | Gln | Thr | Pro<br>390 | Leu | Thr | Tyr | Tyr | Tyr<br>395 | Ser | Leu | Tyr | Phe | Ala<br>400 |
| Thr | Leu | Leu | Leu | His<br>405 | Arg | Gln | Gln | Arg | Asp<br>410 | Glu | His | Lys | Cys | Arg<br>415 | Leu |
| Lys | Tyr | Gly | Glu<br>420 | Asn | Trp | Glu | Glu | Tyr<br>425 | Glu | Arg | Lys | Val | Pro<br>430 | Tyr | Lys |
| Ile | Ile | Pro<br>435 | Tyr | Val | Tyr | | | | | | | | | | |

( 2 ) INFORMATION FOR SEQ ID NO:3:

( i ) SEQUENCE CHARACTERISTICS:
        ( A ) LENGTH: 419 amino acids
        ( B ) TYPE: amino acid
        ( C ) STRANDEDNESS: single
        ( D ) TOPOLOGY: linear ( i i ) MOLECULE TYPE: peptide ( x ) PUBLICATION INFORMATION:
        ( A ) AUTHORS: Worman, H. J.
                  Evans, C. D.
                  Blobel, G.
        ( B ) TITLE: The Lamin B Receptor of the Nuclear Envelope
                 Inner Membrane
        ( C ) JOURNAL: J. Cell Biol.
        ( D ) VOLUME: 111
        ( F ) PAGES: 1535-1542
        ( G ) DATE: 1990
        ( K ) RELEVANT RESIDUES IN SEQ ID NO:3: FROM 190 TO 608

( x i ) SEQUENCE DESCRIPTION: SEQ ID NO:3:

| | | | | | | | | | | | | | | | |
|---|---|---|---|---|---|---|---|---|---|---|---|---|---|---|---|
| Pro<br>1 | Glu | Lys | Pro | Ser<br>5 | Ser | Lys | Thr | Lys | Glu<br>10 | Leu | Glu | Phe | Gly | Gly<br>15 | Arg |
| Phe | Gly | Thr | Phe<br>20 | Met | Leu | Met | Phe | Phe<br>25 | Leu | Pro | Ala | Thr | Val<br>30 | Leu | Tyr |
| Leu | Val | Leu<br>35 | Met | Cys | Lys | Gln | Asp<br>40 | Asp | Pro | Ser | Leu | Met<br>45 | Asn | Phe | Pro |
| Pro | Leu<br>50 | Pro | Ala | Leu | Glu | Ser<br>55 | Leu | Trp | Glu | Thr | Lys<br>60 | Val | Phe | Gly | Val |

-continued

```
Phe  Leu  Leu  Trp  Phe  Phe  Phe  Gln  Ala  Leu  Phe  Tyr  Leu  Leu  Pro  Ile
 65             70                       75                            80

Gly  Lys  Val  Val  Glu  Gly  Leu  Pro  Leu  Ser  Asn  Pro  Arg  Lys  Pro  Gln
               85                        90                       95

Tyr  Arg  Ile  Asn  Gly  Phe  Tyr  Ala  Phe  Leu  Leu  Thr  Ala  Ala  Ala  Ile
              100                      105                      110

Gln  Thr  Leu  Leu  Tyr  Phe  Gln  Phe  Glu  Leu  His  Tyr  Leu  Tyr  Asp  His
          115                      120                      125

Phe  Val  Gln  Phe  Ala  Val  Ser  Ala  Ala  Ala  Phe  Ser  Met  Ala  Leu  Ser
     130                      135                      140

Ile  Tyr  Leu  Tyr  Ile  Arg  Ser  Leu  Lys  Ala  Pro  Glu  Glu  Asp  Leu  Ala
145                      150                      155                      160

Pro  Gly  Gly  Asn  Ser  Gly  Tyr  Leu  Val  Tyr  Asn  Phe  Phe  Thr  Gly  His
               165                      170                           175

Glu  Leu  Asn  Pro  Arg  Ile  Gly  Ser  Phe  Asp  Leu  Lys  Tyr  Phe  Cys  Glu
               180                      185                      190

Leu  Arg  Pro  Gly  Leu  Ile  Gly  Trp  Val  Val  Ile  Asn  Leu  Ala  Met  Leu
          195                      200                      205

Leu  Ala  Glu  Met  Lys  Ile  His  Asn  Gln  Ser  Met  Pro  Ser  Leu  Ser  Met
     210                      215                      220

Ile  Leu  Val  Asn  Ser  Phe  Gln  Leu  Leu  Tyr  Val  Val  Asp  Ala  Leu  Trp
225                      230                      235                      240

Asn  Glu  Glu  Ala  Val  Leu  Thr  Thr  Met  Asp  Ile  Thr  His  Asp  Gly  Phe
               245                      250                      255

Gly  Phe  Met  Leu  Ala  Phe  Gly  Asp  Leu  Val  Trp  Val  Pro  Phe  Val  Tyr
               260                      265                      270

Ser  Leu  Gln  Ala  Phe  Tyr  Ile  Val  Gly  His  Pro  Ile  Ala  Ile  Ser  Trp
          275                      280                      285

Pro  Val  Ala  Ala  Ala  Ile  Thr  Ile  Leu  Asn  Cys  Ile  Gly  Tyr  Tyr  Ile
     290                      295                      300

Phe  Arg  Ser  Ala  Asn  Ser  Gln  Lys  Asn  Asn  Phe  Arg  Arg  Asn  Pro  Ala
305                      310                      315                      320

Asp  Pro  Lys  Leu  Ser  Tyr  Leu  Lys  Val  Ile  Pro  Thr  Ala  Thr  Gly  Lys
               325                      330                      335

Gly  Leu  Leu  Val  Thr  Gly  Trp  Trp  Gly  Phe  Val  Arg  His  Pro  Asn  Tyr
               340                      345                      350

Leu  Gly  Asp  Ile  Ile  Met  Ala  Leu  Ala  Trp  Ser  Leu  Pro  Cys  Gly  Phe
          355                      360                      365

Asn  His  Ile  Leu  Pro  Tyr  Phe  Tyr  Val  Ile  Tyr  Phe  Ile  Cys  Leu  Leu
     370                      375                      380

Val  His  Arg  Glu  Ala  Arg  Asp  Glu  His  His  Cys  Lys  Lys  Lys  Tyr  Gly
385                      390                      395                      400

Leu  Ala  Trp  Glu  Arg  Tyr  Cys  Gln  Arg  Val  Pro  Tyr  Thr  His  Ile  Ser
               405                      410                      415

Leu  His  Leu
```

( 2 ) INFORMATION FOR SEQ ID NO:4:

( i ) SEQUENCE CHARACTERISTICS:
        ( A ) LENGTH: 473 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:

(A) ORGANISM: Saccharomyces cerevisiae (x) PUBLICATION INFORMATION:
   (A) AUTHORS: Chen, W
        Capieaux, E.
        Balzi, E.
        Goffeau, A.
   (B) TITLE: The YGL022 Gene Encodes a Putative Transport Protein
   (C) JOURNAL: Yeast
   (D) VOLUME: 7
   (F) PAGES: 305-308
   (G) DATE: 1991

(xi) SEQUENCE DESCRIPTION: SEQ ID NO:4:

```
Met Ala Lys Asp Asn Ser Glu Lys Leu Gln Val Gln Gly Glu Glu Lys
1               5                   10                  15

Lys Ser Lys Gln Pro Val Asn Phe Leu Pro Gln Gly Lys Trp Leu Lys
            20                  25                  30

Pro Asn Glu Ile Glu Tyr Glu Phe Gly Gly Thr Thr Gly Val Ile Gly
            35                  40                  45

Met Leu Ile Gly Phe Pro Leu Leu Met Tyr Tyr Met Trp Ile Cys Ala
    50                  55                  60

Glu Phe Tyr His Gly Lys Val Ala Leu Pro Lys Ala Gly Glu Ser Trp
65                  70                  75                  80

Met His Phe Ile Lys His Leu Tyr Gln Leu Val Leu Glu Asn Gly Ile
            85                  90                  95

Pro Glu Lys Tyr Asp Trp Thr Ile Phe Leu Thr Phe Trp Val Phe Gln
            100                 105                 110

Ile Ile Phe Tyr Tyr Thr Leu Pro Gly Ile Trp Thr Lys Gly Gln Pro
        115                 120                 125

Leu Ser His Leu Lys Gly Lys Gln Leu Pro Tyr Phe Cys Asn Ala Met
    130                 135                 140

Trp Thr Leu Tyr Val Thr Thr Thr Leu Val Leu Val Leu His Phe Thr
145                 150                 155                 160

Asn Leu Phe Arg Leu Tyr Val Ile Ile Asp Arg Phe Gly Arg Ile Met
            165                 170                 175

Thr Cys Ala Ile Ile Ser Gly Phe Ala Phe Ser Ile Ile Leu Tyr Leu
            180                 185                 190

Trp Thr Leu Phe Ile Ser His Asp Tyr His Arg Met Thr Gly Asn His
        195                 200                 205

Leu Tyr Asp Phe Phe Met Gly Ala Pro Leu Asn Pro Arg Trp Gly Ile
    210                 215                 220

Leu Asp Leu Lys Met Phe Phe Glu Val Arg Leu Pro Trp Phe Thr Leu
225                 230                 235                 240

Tyr Phe Ile Thr Leu Gly Ala Cys Leu Lys Gln Trp Glu Thr Tyr Gly
            245                 250                 255

Tyr Val Thr Pro Gln Leu Gly Val Val Met Leu Ala His Trp Leu Tyr
            260                 265                 270

Ala Asn Ala Cys Ala Lys Gly Glu Glu Leu Ile Val Pro Thr Trp Asp
        275                 280                 285

Met Ala Tyr Glu Lys Phe Gly Phe Met Leu Ile Phe Trp Asn Ile Ala
    290                 295                 300

Gly Val Pro Tyr Thr Tyr Cys His Cys Thr Leu Tyr Leu Tyr Tyr His
305                 310                 315                 320

Asp Pro Ser Glu Tyr His Trp Ser Thr Leu Tyr Asn Val Ser Leu Tyr
            325                 330                 335

Val Val Leu Leu Cys Ala Tyr Tyr Phe Phe Asp Thr Ala Asn Ala Gln
```

|     |     |     | 340 |     |     |     | 345 |     |     |     | 350 |     |     |
|-----|-----|-----|-----|-----|-----|-----|-----|-----|-----|-----|-----|-----|-----|
| Lys | Asn | Ala | Phe | Arg | Lys | Gln | Met | Ser | Gly | Asp | Lys | Thr | Val | Arg | Lys |
|     |     | 355 |     |     |     |     | 360 |     |     |     |     | 365 |     |

```
Lys Asn Ala Phe Arg Lys Gln Met Ser Gly Asp Lys Thr Val Arg Lys
        355                 360                 365

Thr Phe Pro Phe Leu Pro Tyr Gln Ile Leu Lys Asn Pro Lys Tyr Met
    370                 375             380

Val Thr Ser Asn Gly Ser Tyr Leu Leu Ile Asp Gly Trp Tyr Thr Leu
385             390                 395                     400

Ala Arg Lys Ile His Tyr Thr Ala Asp Trp Thr Gln Ser Leu Val Trp
            405                 410                     415

Ala Leu Ser Cys Gly Phe Asn Ser Val Phe Pro Trp Phe Phe Pro Val
            420                 425                 430

Phe Phe Leu Val Val Leu Ile His Arg Ala Phe Arg Asp Gln Ala Lys
        435                 440                 445

Cys Lys Arg Lys Tyr Gly Lys Asp Trp Asp Glu Tyr Cys Lys His Cys
    450                 455                 460

Pro Tyr Val Phe Ile Pro Tyr Val Phe
465                 470
```

( 2 ) INFORMATION FOR SEQ ID NO:5:

( i ) SEQUENCE CHARACTERISTICS:
        ( A ) LENGTH: 453 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Schizosaccharomyces pombe ( x ) PUBLICATION INFORMATION:
        ( A ) AUTHORS: Shimanuki, M.
                Goebl, M.
                Yanagida, M.
                Toda, T.
        ( B ) TITLE: Fission Yeast sts1+Gene Encodes a Protein
                Similar to the Chicken Lamin B Receptor
        ( C ) JOURNAL: Molecular Biology of the Cell
        ( D ) VOLUME: 3
        ( F ) PAGES: 263-273
        ( G ) DATE: 1992

( x i ) SEQUENCE DESCRIPTION: SEQ ID NO:5:

```
Met Lys Ser Thr Val Lys Lys Ser Ala Pro Arg Glu Phe Gly Gly Ala
1               5               10              15

Lys Gly Ala Leu Ala Ile Met Thr Gly Phe Pro Cys Leu Met Tyr Tyr
            20              25              30

Leu Trp Ala Cys Ser Lys Phe Asn Asp Ser Gln Phe Ile Lys Pro Glu
        35              40              45

Ser Phe Thr Ile Ala Gly Phe Gln Asn Phe Phe Arg Thr Leu Gly His
    50              55              60

Tyr Ile Tyr Val Gly Ala Tyr Pro Thr Arg Tyr Ala Phe Leu Val Phe
65              70              75              80

Trp Ser Phe Cys Ile Val Gln Ala Val Met Tyr Leu Thr Leu Pro Gly
            85              90              95

Val Arg Thr Gln Gly Leu Pro Leu Lys His Arg Asn Asn Glu Arg Leu
            100             105             110

Pro Tyr Leu Cys Asn Ala Ile Trp Ser Phe Tyr Thr Thr Ile Val Ile
        115             120             125

Leu Ala Val Leu His Val Thr His Val Phe Pro Ile Thr Thr Phe Ile
    130             135             140
```

| | | | | | | | | | | | | | | |
|---|---|---|---|---|---|---|---|---|---|---|---|---|---|---|
| Asp | Met | Phe | Gly | Pro | Leu | Met | Ser | Val | Ala | Ile | Ile | Thr | Ala | Phe | Val |
| 145 | | | | | 150 | | | | | 155 | | | | | 160 |
| Cys | Thr | Phe | Val | Leu | Tyr | Thr | Gly | Thr | Leu | Leu | Phe | Gly | Asp | Arg | Leu |
| | | | | 165 | | | | | 170 | | | | | 175 | |
| Phe | Asp | Lys | Pro | His | Arg | Leu | Ser | Gly | Asn | Pro | Ile | Tyr | Asp | Ala | Phe |
| | | | 180 | | | | | 185 | | | | | 190 | | |
| Met | Gly | Ala | Cys | Leu | Asn | Pro | Arg | Leu | Gly | Lys | Leu | Leu | Asp | Phe | Lys |
| | | 195 | | | | | 200 | | | | | 205 | | | |
| Met | Phe | Phe | Glu | Val | Arg | Ile | Pro | Trp | Phe | Ile | Leu | Phe | Phe | Ile | Ser |
| | 210 | | | | | 215 | | | | | 220 | | | | |
| Val | Gly | Ala | Ala | Val | Arg | Gln | Tyr | Glu | Thr | Tyr | Gly | Thr | Val | Ser | Pro |
| 225 | | | | | 230 | | | | | 235 | | | | | 240 |
| Gln | Val | Leu | Phe | Val | Cys | Leu | Gly | His | Tyr | Leu | Tyr | Ala | Asn | Ala | Cys |
| | | | | 245 | | | | | 250 | | | | | 255 | |
| Ser | Lys | Gly | Glu | Gln | Leu | Ile | Val | Pro | Thr | Trp | Asp | Met | Ala | Tyr | Glu |
| | | | 260 | | | | | 265 | | | | | 270 | | |
| Lys | Phe | Gly | Phe | Met | Leu | Ile | Phe | Trp | Asn | Met | Ala | Gly | Val | Pro | Phe |
| | | 275 | | | | | 280 | | | | | 285 | | | |
| Thr | Tyr | Ser | His | Cys | Thr | Leu | Tyr | Leu | Phe | Ser | His | Asp | Pro | Ser | Val |
| | 290 | | | | | 295 | | | | | 300 | | | | |
| Tyr | Asn | Trp | Ser | Thr | Gln | Tyr | Thr | Thr | Gly | Ile | Tyr | Val | Leu | Leu | Leu |
| 305 | | | | | 310 | | | | | 315 | | | | | 320 |
| Cys | Cys | Tyr | Tyr | Ile | Phe | Asp | Thr | Cys | Asn | Gly | Gln | Lys | Asn | His | Phe |
| | | | | 325 | | | | | 330 | | | | | 335 | |
| Arg | Asn | Gln | Ile | Tyr | Gly | Thr | Glu | Val | His | Arg | Lys | Thr | Phe | Pro | Gln |
| | | | 340 | | | | | 345 | | | | | 350 | | |
| Leu | Pro | Trp | Leu | Ile | Ile | Lys | Asn | Pro | Thr | Phe | Ile | Arg | Cys | Ala | Asn |
| | | 355 | | | | | 360 | | | | | 365 | | | |
| Gly | Gly | Thr | Leu | Leu | Thr | Ser | Gly | Trp | Tyr | Arg | Tyr | Ala | Arg | Lys | Ile |
| | 370 | | | | | 375 | | | | | 380 | | | | |
| His | Tyr | Thr | Ala | Asp | Phe | Phe | Gln | Ser | Leu | Ser | Trp | Ala | Leu | Ile | Thr |
| 385 | | | | | 390 | | | | | 395 | | | | | 400 |
| Gly | Phe | Gln | Ser | Pro | Leu | Pro | Tyr | Phe | Tyr | Pro | Ser | Phe | Phe | Phe | Val |
| | | | | 405 | | | | | 410 | | | | | 415 | |
| Val | Leu | Val | His | Arg | Val | Ser | Arg | Asp | Ile | Lys | Lys | Cys | Lys | Ala | Lys |
| | | | 420 | | | | | 425 | | | | | 430 | | |
| Tyr | Gly | Ala | Asp | Phe | Asp | Glu | Tyr | Asp | Arg | Ile | Cys | Pro | Tyr | Leu | Phe |
| | | 435 | | | | | 440 | | | | | 445 | | | |
| Ile | Pro | Tyr | Ile | Phe | | | | | | | | | | | |
| | 450 | | | | | | | | | | | | | | |

BIBLIOGRAPHY

Ashman, W. H., et al., *Lipids* 26: 628–632 (1991).
Baloch, R. and Mercer, I., *Phytochemistry* 26: 663–668 (1987).
Balzi, E., et al., *J. Biol. Chem.* 262: 16871–16879 (1987).
Brugge, J. S., et al., *Mol. Cell. Biol.* 7:2180–2187 (1987).
Chen, W., et al., *Yeast* 7: 305–308 (1991).
Gaber, R. F., et al., *Mol. Cell. Biol.* 9: 3447–3456 (1989).
Kyte, J., and Doolittle, R. F., *J. Mol. Biol.* 157: 105–132 (1982).
Lorenz, T., and Parks, L. W., *DNA and Cell Biol.* 11: 685–692 (1992).
Marcireau, C., et al., *Curr. Genet.* 22: 267–272 (1992).
Molzahn, S. W., and Woods, R. A., *J. Gen Microbiol.* 72: 339–348 (1972).
Nasmyth, K. A., and Tatcheil, K., *Cell* 19: 753–764 (1980).
Paltauf, F., et al., in Jones, E. W., et al., eds., *The Molecular and Cellular Biology of the Yeast Saccharomyces, Gene Expression*, Cold Spring Harbor Laboratory Press, 1992, pages 415, 418–420, 424–428, and 434–437.
Shimanuki, M., et al., *Mol. Biol. Cell* 3: 263–273 (1992).
Worman, H. J., et al., *J. Cell Biology* 111: 1535–1542 (1990).

We claim:

1. A purified and isolated DNA fragment of *Saccharomyces cerevisiae* (*S. cerevisiae*) comprising a DNA sequence encoding *S. cerevisiae* sterol Δ14 reductase.

2. The purified and isolated DNA fragment according to claim 1, wherein the fragment comprises a DNA sequence which hybridizes under stringent conditions with a sequence encoding *S. cerevisiae* sterol Δ14 reductase.

3. The purified and isolated DNA fragment according to claim 2, wherein the fragment comprises a DNA sequence which hybridizes under stringent conditions with the nucleotides numbered 419 to 1732 of SEQ ID NO. 1.

4. The purified and isolated DNA fragment according to claim 2, wherein the DNA fragment comprises a DNA sequence encoding *S. cerevisiae* sterol Δ14 reductase having the amino acid sequence as depicted in residues numbered 1 to 38 of SEQ ID NO. 2.

5. An isolated and purified RNA sequence corresponding to a DNA sequence according to claim 1.

6. A biologically functional plasmid or vital DNA vector containing the purified and isolated DNA fragment of *S. cerevisiae* comprising the DNA sequence according to claim 1.

7. The plasmid or vital DNA vector according to claim 6, wherein the plasmid contains a purified and isolated DNA fragment of *S. cerevisiae* comprising a DNA sequence which hybridizes under stringent conditions with a sequence encoding *S. cerevisiae* sterol Δ14 reductase.

8. The plasmid or vital DNA vector according to claim 7, wherein the plasmid contains a purified and isolated fragment of *S. cerevisiae* comprising a DNA sequence which hybridizes under stringent conditions with the nucleotides numbered 419 to 1732 of SEQ ID NO. 1.

9. A procaryotic or eucaryotic host cell transformed or transfected with the plasmid or vector according to claim 6 in a manner allowing the host cell to express the polypeptide encoded by the DNA.

10. The host cell according to claim 9 wherein the host cell is a *S. cerevisiae* strain.

11. A procaryotic or eucaryotic host cell transformed or transfected with the plasmid or vector according to claim 7 in a manner allowing the host cell to express the polypeptide encoded by the DNA.

12. The host cell according to claim 11 wherein the host cell is a *S. cerevisiae* strain.

13. A *S. cerevisiae* strain according to claim 12 which produces sterol Δ14 reductase in an amount greater than a *S. cerevisiae* strain into which the sterol Δ14 reductase DNA sequence has not been introduced.

* * * * *

UNITED STATES PATENT AND TRADEMARK OFFICE
CERTIFICATE OF CORRECTION

PATENT NO. : 5,512,472
DATED : April 30, 1996
INVENTOR(S) : Lai et al.

It is certified that error appears in the above-indentified patent and that said Letters Patent is hereby corrected as shown below:

Column 7, line 55, "hericide" should read -- herbicide--.
Column 7, line 66, "Tatcheil" should read -- Tatchell--.
Table 3, data line 1, --14-- (not "4") should appear under "Other Sterol".
Column 29, line 11, "38" should read -- 438 --.

Signed and Sealed this

Fifteenth Day of October, 1996

Attest:

BRUCE LEHMAN

*Attesting Officer*  *Commissioner of Patents and Trademarks*